United States Patent [19]

Taylor et al.

[11] Patent Number: 4,917,675
[45] Date of Patent: Apr. 17, 1990

[54] FOLDED FLANGE SEALED SANITARY NAPKIN

[75] Inventors: Martha K. Taylor, Mercerville; Wassim Seidy, Somerset; Subramani Srinivasan, East Brunswick, all of N.J.

[73] Assignee: McNeil-PPC, Inc., Milltown, N.J.

[21] Appl. No.: 219,430

[22] Filed: Jul. 14, 1988

[51] Int. Cl.⁴ ............................................. A61F 13/16
[52] U.S. Cl. ............................... 604/385.1; 206/632; 206/440
[58] Field of Search .................. 604/385 R; 206/632, 206/440

[56] References Cited

U.S. PATENT DOCUMENTS

| | | | |
|---|---|---|---|
| 3,724,651 | 4/1973 | Link | 206/56 AA |
| 3,938,659 | 2/1976 | Wardwell | 206/439 |
| 3,973,567 | 7/1976 | Srinivasan et al. | 604/385 R |
| 4,549,653 | 10/1985 | Lauritzen | 206/441 |
| 4,555,022 | 11/1985 | Eagon et al. | 206/440 |
| 4,556,146 | 12/1985 | Swanson et al. | 206/440 |
| 4,564,108 | 1/1986 | Widlund et al. | 206/438 |
| 4,605,403 | 7/1986 | Tucker | 604/385 R |
| 4,735,316 | 4/1988 | Froidh et al. | 206/438 |
| 4,738,678 | 4/1988 | Paulis | 604/385 R |
| 4,753,647 | 6/1988 | Curtis | 604/385 R |
| 4,787,380 | 11/1988 | Scott | 128/156 |
| 4,807,613 | 2/1989 | Kochnke et al. | 128/155 |
| 4,815,457 | 3/1989 | Mazars et al. | 128/155 |
| 4,848,572 | 7/1989 | Herrera | 206/440 |

*Primary Examiner*—C. Fred Rosenbaum
*Assistant Examiner*—Mark O. Polutta

[57] ABSTRACT

A sanitary napkin is disclosed with flange sealing means for protecting the body-facing surface from dirt and deformation until the napkin is ready for use. The seal is provided by a wrapping member which extends over at least a portion of the absorbent element of the napkin. Upon folding the napkin about a transverse axis, the wrapping member is adhered to itself by an adhesive to protect the napkin.

4 Claims, 1 Drawing Sheet

FOLDED FLANGE SEALED SANITARY NAPKIN

FIELD OF THE INVENTION

This invention relates to protective, absorbent liners for undergarments and the manner in which these liners are individually wrapped for cleanliness prior to use.

BACKGROUND OF THE INVENTION

Traditionally, sanitary napkins have been bundled with several napkins to each package. This single, large package provides a means for keeping all the napkins clean, sanitary and undamaged. Unfortunately, however, once the napkins are removed from the package and carried individually in a pocket or purse, they are virtually unprotected from dirt and deforming pressures.

Recently, this problem has been diminished by individually wrapping folded napkins. Specifically, many of today's napkins are provided with an outer wrap, usually made of paper, which is customarily sealed around the napkin and can be easily taken off by the user at the time the napkin is used. This method of wrapping protects the enclosed napkin from dirt and deformation until it is removed, and because the napkin is folded into a compact size, it becomes more convenient to carry. Yet, individually wrapping sanitary napkins typically increases manufacturing costs associated with the requisite materials and processing of these wraps. This expense can result, ultimately, in an increased cost of the product to the consumer.

Although not specifically addressing the problem of the additional expense of a separate outside wrapper, Werner, U.S. Pat. No. 3,688,771 teaches a sanitary napkin that comprises free ends of a protective strip that extend around the extremities of the napkin and are folded over the top surface. Werner discloses that the free ends are used in this embodiment to cover and protect the body-contacting surface of the pad from inadvertent soilage before use. The protective strip of this device also serves as a means for covering the attachment adhesive means of the napkin.

Werner suggests an alternative means for protecting a napkin. However, there is no teaching for the elimination of the outer wrap. This patent also fails to disclose the benefits of folding the napkin to provide a discreet way of carrying it before use. Moreover, since there is no teaching for fixing or adhering the free ends of Werner s product after folding them over the top surface of the napkin, the degree of cleanliness this embodiment provides is questionable.

Accordingly, there is still a need for a napkin with wrapping means that provides for individual wrapping without added manufacturing and material costs. There is also a need for a less expensive napkin that can be discreetly stored until use which is also resistant to contamination and deforming pressures.

SUMMARY OF THE INVENTION

A sanitary napkin is herein provided with sealing means for individually wrapping the napkin prior to use. The napkin has an elongated wrapping member having portions that extend over portions of the edges of the absorbent element of the napkin. These extended areas form opposing outwardly extending flanges portions. Disposed on these flange portions is pressure-sensitive adhesive means for adhering one region of the wrapping member to a correspondingly disposed region of an opposing flange portion to retain the napkin in its folded position prior to use. Accordingly, this invention teaches a novel napkin with wrapping means that provides for individual wrapping without the need of an additional outer paper wrapping material. Moreover, since the product is folded into a compact shape, it can be discreetly stored until use. Moreover, the napkin of this invention is relatively easy to use and provides resistance to contamination and deforming pressures, while at the same time, eliminates the additional manufacturing time and material associated with an outer paper wrapping member.

In the preferred embodiment of this invention, the wrapping member has flange portions that extend over the edges of the napkin to form a continuous, outwardly extending flange around the perimeter of the absorbent element of the napkin. This embodiment also includes adhesive means that is disposed continuously about the perimeter of this outwardly extending flange, so when the napkin is folded about a transverse axis and self-sealed, it can be protected from contamination of its body-facing side. Also provided on this novel napkin are tabs for enabling a user to grip the wrapping member to separate the adhesive means adhering the flange portions together. The napkin of this invention can also comprise resilient material for helping the napkin to unfold after it has been opened.

Included with this invention, is a novel method for individually wrapping a sanitary napkin. The method applies an elongated wrapping member to the adhesive-bearing side of a conventional absorbent element. The wrapping member is selected to comprise a portion that extends over a portion of the edges of the absorbent element to form opposing outwardly extending flange portions. Next, the napkin is folded onto its body-facing side along at least a transverse axis of the napkin and pressure-sensitive adhesive means is used to adhere the flange portions together to retain the napkin in its folded position prior to use.

It is, therefore, an object of this invention to provide a sanitary napkin having a flanged wrapping means that protects the adhesive-bearing side of the napkin and also serves as a means for protecting the body-facing side of the napkin.

It is another object of this invention to provide a sanitary napkin that does not require a separate paper outer wrapping material.

It is still another object of this invention to provide a sanitary napkin that can be wrapped into a compact size and discreetly stored until use.

It is still another object of this invention to provide a sanitary napkin that is resistant to deforming pressures.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode for the best practical application of the principles thereof, and in which.

DETAILED DESCRIPTION OF THE INVENTION

Figure 1:
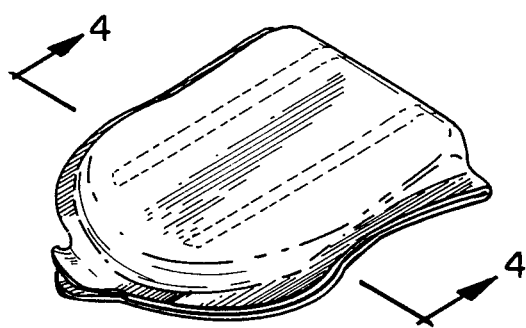
FIG. 1: is a perspective view of the sanitary napkin of this invention illustrating how the napkin appears prior to use.

In accordance with the teachings of this invention, a sanitary napkin with novel sealing means for individually wrapping the napkin prior to use is herein provided. The napkin comprises an absorbent element having a body-facing side, and adhesive-bearing side, longitudinally extending edges and transverse edges. The absorbent element is folded along a transverse axis to overlap portions of the body-facing side in its "as packaged" condition. Disposed over the adhesive-bearing side of the absorbent element, is an elongated wrapping member having an interior surface for contacting the adhesive on the absorbent element. This wrapping member has portions that extend over portions of the edges of the absorbent element to form opposing outwardly flange portions. Disposed at a location on the interior surface of the flange portions, is pressure-sensitive adhesive means for adhering one flange portion of the wrapping member to a correspondingly disposed region on the inner surface of an opposing flange portion to retain the napkin in its folded position prior to use. The sanitary napkin of this invention can also comprise adhesive means disposed on a plurality of locations about the perimeter of the flange portions, or alternatively, adhesive means disposed continuously about the perimeter of the flange portions. This invention also contemplates trimming the wrapping member and its flange portions so that each flange portion comprises a tab for enabling a user to grip the wrapping member to separate the adhesive means adhering the flange portions together prior to using the napkin. Ideally, the tabs of this invention are arranged to face each other when the napkin is folded. The napkin of this invention also can include the resilient material for helping the napkin to unfold after it has been opened. Finally, in a more preferred embodiment of this invention, the flange portions extend over the edges of the napkin to form a continuous, outwardly extending flange around the perimeter of the absorbent element. In this embodiment adhesive means can be disposed continuously about the perimeter of the outwardly extending flange so that the napkin is substantially sealed to prevent soiling prior to use.

In one preferred embodiment of this invention, the sanitary napkin of this invention has disPosed on the adhesive-bearing side of the absorbent element a wrapping member formed as a folded bag. The folded bag may be made of any suitable sheet-like material that can be folded and sealed at one transverse edge and at a longitudinal seam to form a bag or receptacle member. The receptacle member should be slightly larger around its perimeter than the absorbent element so as to form a flange portion around the perimeter of the absorbent element. The receptacle member may contain a soft, pliable fabric which can be saturated with fluid and is suitable for wiping and/or cleaning the perineal and/or vaginal area when removing a sanitary napkin after use. This vaginal wipe may be made of any suitable woven or nonwoven fabric or paper product capable of retaining an aqueous solution or other solution known to those of ordinary skill in the art suitable for cleansing the perineum. The receptacle member should be sealed around its perimeter interior to the flange portion such that when the flange portion is removed, the receptacle remains intact.

The receptacle means is preferably attached to the absorbent element with pressure sensitive adhesive. The entire construction can be folded along the longitudinal edges around the absorbent element in a so-called "C-fold" and sealed around the longitudinal sides of the absorbent element. The seal may be made mechanically, ultrasonically, radiantly or using any means to seal known to those of ordinary skill in the art. Alternatively, the construction may be folded transversely along the midpoint of the longitudinal axis of the absorbent element to form a flange portion and sealed around the flange portion.

When the seal is broken, the receptacle means and vaginal wipe remain intact. The vaginal wipe may be used to cleanse the perineum and the receptacle means may be used to dispose of the used napkin and vaginal wipe.

The novel method, as herein provided, individually wraps a sanitary napkin by first providing an absorbent element having longitudinally extending edges and transverse edges. Then the method applies an elongating wrapping member to the adhesive-bearing side of absorbent element. The wrapping member of this method is selected to comprise a portion that extends over a portion of the edges of the absorbent element to form opposing outwardly extending flange portions. Next, the method folds the napkin onto its body-facing side along at least a transverse axis, whereupon the flange portions are adhered using pressure-sensitive adhesive means to retain the napkin in its folded position prior to use.

Figure 2:
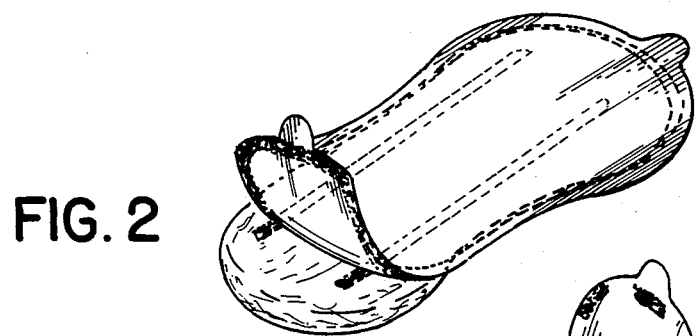
FIG. 2: is a perspective view of the sanitary napkin taken from the garment facing side illustrating how the napkin can be opened to expose its body-facing side and also, how the elongated wrapping member can be released from the adhesive means of the absorbent element.
Figure 3:
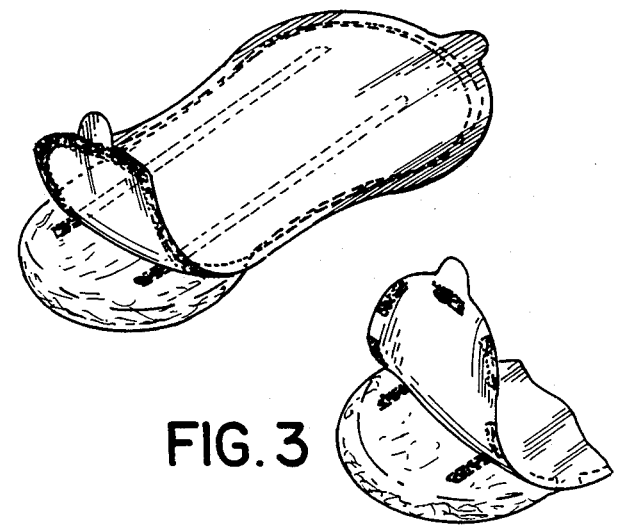
FIG. 3: is a perspective of an alternate embodiment for the adhesive as it is applied to the flange portions of the elongated wrapping member.
Figure 4:
FIG. 4: is a transverse cross-sectional view of the napkin of FIG. 1, taken through line 4—4.

FIGS. 1-4 illustrate, in perspective and transverse cross-section, a sanitary napkin 10, embodying the teachings of this invention. The napkin 10 comprises, as depicted in FIGS. 2 and 4, an absorbent element 24 having a body-facing side, and an adhesive-bearing side, longitudinally extending edges and transverse edges. The absorbent element 24 is folded along at least a transverse axis to overlap portions of the body-facing side. Provided on the adhesive-bearing side of the absorbent element 24 is an elongated wrapping member 33 having an interior surface disposed over said adhesive-bearing side of said absorbent element 24. The wrapping member 33 has portions that extend over portions of the edges of the absorbent element 24 to form opposing outwardly extending flange portions 16 and 17. Pressure-sensitive adhesive means 32 is disposed at a location on said interior surface of said flange portions 16 and 17 for adhering one flange portion of said wrapping member to a correspondingly disposed region on the interior surface of an opposing flange portion to retain said napkin 10 in its folded position prior to use, as depicted in FIG. 1. The pressure-sensitive adhesive means may be disposed on a plurality of locations 34, as illustrated in FIG. 3. The pressure-sensitive adhesive means may also be disposed continuously around the perimeter 32 of the flange portion 16 and 17. As depicted in FIGS. 1-3, the flange portions of the novel napkin of this invention can each comprise a tab 12 and 14 for enabling a user to grip the wrapping member 33 to separate the adhesive means 32 or 34 disposed on said flange portions 16 and 17 prior to using the napkin 10. The tabs 12 and 14 can be arranged to face each other when the napkin is in a folded position, as illustrated in FIG. 1. In a preferred embodiment of this invention the absorbent element 24 comprises resilient material for helping the napkin 10 to unfold after it has been opened. Finally, in a more preferred embodiment of this invention the flange portion 16 and 17 extend over the edges of the napkin to form a continuously outwardly extending flange substantially like that described in FIGS. 1–4. The flange of this embodiment extends around the perimeter of the absorbent element 24 and preferably has pressure-sensitive adhesive means disposed continuously about its perimeter.

The method of this invention initially provides an absorbent element 24 having a body-facing side, an adhesive-bearing side, longitudinally extending edges, and transverse edges. Next, the method applies an elongated wrapping member 33 having an interior surface to said adhesive-bearing side of said absorbent element 24. This elongated wrapping member 33 is arranged so that its interior surface is adhered with the adhesive-bearing side of the absorbent element 24. The wrapping member 33 is selected to comprise a portion that extends over a portion of the edges of the absorbent element 24 to form opposing outwardly extending flange portions 16 and 17. These flange portions 16 and 17 are provided with pressure-sensitive adhesive means disposed at a location on the interior surface of these flange portions 16 and 17. Finally, the method folds the napkin 10 onto its body-facing side along at least a transverse axis of the napkin 10, where upon the pressure-sensitive adhesive means on said location on the interior surface of the wrapping member 33 adheres the flange portion 16 and 17 to retain the napkin 10 in its folded position prior to use. Alternatively, in a more preferred method of this invention, the flange portions 16 and 17 are provided with pressure-sensitive adhesive means on a plurality of locations 34 about the perimeter of said flange portions 16 and 17, such that when the napkin 10 is folded about a transverse axis, these pressure-sensitive adhesive means on a plurality of locations 34 adhere the flange portions 16 and 17 to one another to retain the napkin 10 in the folded position prior to use. It is anticipated that this method could also provide pressure-sensitive adhesive means disposed continuously about the perimeter 32 such that when the napkin 10 folded, the pressure-sensitive adhesive means adheres the flange portions 16 and 17 to one another to retain the napkin in its folded position. The method of this invention also anticipates utilizing flange portions 16 and 17 comprising their own tabs 12 and 14 for enabling a user to grip the wrapping member 33 to separate the pressure-sensitive adhesive means adhering the flange portions 16 and 17 together. Additionally, this method can provide tabs 12 and 14 that are selected to face each other when the napkin 10 is folded about a transverse axis. Again, as in the novel product itself, the absorbent element 24 can be selected to comprise resilient material for helping the napkin 10 to unfold after it has been opened.

The absorbent element 24 of this invention should be made of soft, comfortable material. Adequate absorbency may be built into the core of the absorbent without adding bulk by adding super absorbent materials, now known, which have the properties of high-liquid retention, e.g. cross-linked acrylate polymers. The absorbent element 24 should retain fluid well without allowing it to squeeze out and re-wet the wearer. In one preferred embodiment of this invention, the absorbent element 24 contains conventional resilient materials for enabling the napkin 10 to unfold easily after it has been opened. The resilient material should be flexible without subtracting significantly from user's comfort. Such materials include compacted cellulosic fibers and hydrocolloidal materials such as those described by Kopolow, U.S. Pat. No. 4,551,142. Alternatively, compressed cottony pulp fibers, rayon, staple-length synthetic fibers and/or filaments of thermoplastic polymers or elastomers can be used for this purpose. It is expected that many shapes, sizes and materials will become apparent to those in the art for enabling the napkin to more readily bounce-back after opening. Generally, the absorbent element 24 should be about 4–10 inches in length, preferably about 6–9 inches. As described in FIG. 4, the absorbent element 24 comprises a core 28 which preferably is made of loosely associated absorbent hydrophilic materials such as cellulose fibers, wood pulp, regenerated cellulose or cotton fibers, and/or other materials generally known in the art. Such fibers may be chemically or physically modified and the core may include such fibers in combination with other materials, both natural and synthetic, such as hydrophilic foams, hydrophilic polymers or the like. For the preferred embodiment of this invention, wood pulp is the material of choice because of its availability and inexpensive costs.

As is customary in the art, covering the side of the napkin to be worn against the body of the user, is a body fluid pervious surface 35. This surface may be any woven or non-woven material pervious to body fluid contacting its surface. The body-facing material should be soft and easily permeated by body fluids. Preferably, it should be a material which allows the passage of fluid without moving it appreciably in its horizontal plane. Furthermore, it should retain little or no fluid in its structure to provide a relatively dry surface next to the skin. Generally, the fluid permeable surface 35 is a single, rectangular sheet of material having a width sufficient to cover the body-facing side of the absorbent element 24. Preferably, the fluid pervious surface 35 is longer than the core 28 so as to form end tabs, which may sealed to fully enclose the core 28. The fluid pervious surface 35 is generally made of well-known cellulosic material such as cotton, rayon or wood pulp. Also, the body fluid pervious surface 35 ideally comprises fibers or filaments of thermo-plastic polymers such as polyethylene or polypropylene.

The sanitary napkin 10 of this invention further includes a body fluid impervious surface 31 on the body-facing side of the absorbent element 24. The impervious surface 31 should be made from fluid impermeable materials such as polyethylene or a non-woven material coated with an impermeable film. The impervious surface should allow the passage of air and moisture vapor while substantially blocking the passage of fluid to the outer surface. The impervious surface 31 in the preferred embodiment is sealed together with the pervious surface 35 around the perimeter of the absorbent element 24 to prevent leakage of fluid from the sides of the absorbent element 24.

The impervious surface 31 may be heat sealed or fastened by way of adhesives to the core 28 or to the core 28 wrapped in a pervious surface cover. The impervious surface 31 may comprise any thin, flexible, body fluid impermeable material such as, a polymeric film, e.g. polyethylene, polypropylene, cellophane or even a normally fluid pervious material that has been treated to be impervious such as impregnated fluid repellent paper. The fluid impervious layer 31 is generally fastened to the core 28 by means of a plurality of longitudinally extending lines of adhesive. Preferably, however, the impervious surface 31 is heat bondable material such as polyethylene which may be bonded to the pervious surface 35 to completely enclose the core material 28.

An important aspect of this invention is the elongated wrapping member 33. Traditionally, the prior art has used release paper only to protect the adhesive means of the absorbent element 24. One important aspect of this invention is that the elongated wrapping member 33 not only protects the adhesive strips 18 and 20, but also may be adhered around a folded napkin to protect the body-facing side of the napkin as depicted in FIG. 1. The elongated wrapping member 33 of this invention may be made of any suitable sheet-like material which adheres with sufficient tenacity to the adhesive means, i.e. strips 18 and 20, to remain in place, but which can be readily removed when the napkin 10 is to be used. Conventional materials used for this purpose include woven webs, non-woven bonded fiber webs, non-woven thread webs, thread reinforced non-woven webs, plastic films, i.e., polyethylene or polypropylene, and/or laminates of the above. A particularly useful material for this member 33 is a semi-bleached kraft paper, the adhesive contacting side, or releasable surface, of which has been silicone-coated to provide easier removal from the adhesive 18 and 20 on the absorbent element 24.

The adhesive materials used for adhesive means 18, 20, 32 and/or 34 should be made of any known pressure-sensitive adhesive material. As used herein, the term "pressure-sensitive" refers to any releasable adhesive or releasable tenacious means. Adhesive compositions suitable for sanitary napkins include, for example, the water-based pressure-sensitive adhesives such as the acrylate adhesives, e.g. vinyl acetate-2 ethyl hexyl acetate copolymer which is generally combined with tackifiers such as, for example, ethylene amine. Alternatively, the adhesive may comprise the rapid setting thermoplastic (hot-melt) adhesives. The adhesive elements may also comprise a 2-sided adhesive tape. It is also anticipated that adhesives based on an elastomer selected from natural or synthetic rubbers could be used.

Two embodiments are illustrated in FIGS. 2 and 3 for providing adhesive to the flange portions 16 and 17 of the elongated wrapping member 33. FIG. 2 illustrates an embodiment wherein the adhesive means 32 is disposed continuously around the perimeter of the elongated wrapping member 33. FIG. 3 illustrates, alternatively, a preferred embodiment wherein the adhesive means 34 is disposed on a plurality of locations about the perimeter of the flange portions 16 and 17. These embodiments are illustrated for example only, and it is expected that those skilled in the art will find variations readily apparent. In either of the preferred situations, the purpose of the adhesive means 32 or 34 is to provide a means for adhering the napkin after it is folded onto its body-facing side to protect the napkin 10 within the wrapping member 33 until needed for use. When the adhesive is disposed on a plurality of spaced locations, the napkin may be folded about a transverse axis so that one flange portion can be adhered to a correspondingly disposed region on the interior surface of an opposing flange portion to retain the napkin 10 in a folded position. Ideally these adhesive means 34 are aligned with one another to provide a more complete seal. When the adhesive is disposed continuously about the perimeter of the flange portions 16 and 17, the napkin 10 can be folded in similar fashion to engage the adhesive means on the flange portion 16 with the adhesive means on the flange portion 17. Special care should be taken in applying the adhesive to the wrapping member 33 during manufacture, so as to not apply adhesive to the gripping tabs 12 and 14, when they are included with the product.

Referring back to FIG. 1, a preferred embodiment is depicted in transverse view illustrating the napkin 10 as it appears to the user prior to applying it to the body. The absorbent element 24 is safely protected from dirt and contamination by the sealed flange portion 16 and 17. There is no outside paper wrapping, so there is less waste associated with using this product. In accordance with one embodiment of this invention, tabs 12 and 14 may be gripped by the user and the napkin 10 may be opened for use with minimal force. After opening the napkin 10, the user can peel the elongated wrapping member 33 away from the adhesive-bearing side of the absorbent element 24 as shown in FIG. 2. The napkin 10 then can be inserted into the crotch of an undergarment.

From the foregoing, it can be realized that this invention provides an improved sanitary napkin with wrapping means that provides individual wrapping without added manufacturing and material costs. A method of wrapping this sanitary napkin is also provided which is convenient and provides more protection than prior art unwrapped napkins. An important aspect of this invention is that the outside wrapping member can be eliminated without any loss in cleanliness or convenience. Although various embodiments have been illustrated, this was for the purpose of describing, but not limiting the invention. Various modifications, which will become apparent to one skilled in the art, are within the scope of this invention described in the attached claims.

We claim:

1. A sanitary napkin with sealing means for individually wrapping said napkin prior to use comprising:
   (a) an absorbent element having a body-facing side, an adhesive-bearing side, longitudinally extending edges and transverse edges, said element being folded along a transverse axis to overlap portions of said body-facing side;
   (b) an elongated wrapping member having an interior surface disposed over said adhesive-bearing side of said absorbent element, said wrapping member having portions that extend over portions of said edges of said absorbent element to form opposing outwardly extending flange portions;
   (c) pressure-sensitive adhesive means disposed at a location on said interior surface of said flange portions for adhering one flange portion of said wrapping member to a correspondingly disposed region on the interior surface of an opposing flange portion to retain said napkin in its folded position prior to use; and
   (d) wherein said flange portions each comprise a tab for enabling the use to grip said wrapping member to separate said adhesive means adhering said flange portions prior to suing said napkin, and said flange portions extend over the edges of said napkin to form a continuous, outwardly extending flange around the perimeter of said absorbent element, said wrapping member serving also as release paper for the adhesive bearing side of said absorbent element.

2. The sanitary napkin of claim wherein said pressure-sensitive adhesive means is disposed on a plurality of locations about the perimeter of said flange portions.

3. The sanitary napkin of claim 1 wherein said adhesive means is disposed continuously about the perimeter of said flange portions.

4. A method for individually wrapping a sanitary napkin comprising:
 (a) providing an absorbent element having a body-facing side, an adhesive-bearing side, longitudinally extending edges and transverse edges;
 (b) applying an elongated wrapping member having an interior surface to said adhesive-bearing side of said absorbent element, said interior surface being adhered with said adhesive-bearing side of said absorbent element, said wrapping member being selected to comprise a portion that extends over a portion of said edges of said absorbent element to form opposing outwardly extending flange portions, said flange portions being provided with pressure-sensitive adhesive means disposed at a location on said interior surface of said flange portions; and
 (c) folding said napkin onto its body-facing side along at least a transverse axis of said napkins, whereupon said pressure-sensitive adhesive means on said location on said interior surface adheres said flange portions to retain said napkin in its folded position prior to use.

* * * * *

UNITED STATES PATENT AND TRADEMARK OFFICE
CERTIFICATE OF CORRECTION

PATENT NO. : 4,917,675

DATED : April 17, 1990

INVENTOR(S) : Martha K. Taylor et al.

It is certified that error appears in the above-identified patent and that said Letters Patent is hereby corrected as shown below:

Claim 2, column 9, line 5, change "claim wherein" to --claim 1 wherein--.

Signed and Sealed this

Thirteenth Day of October, 1992

Attest:

DOUGLAS B. COMER

Attesting Officer	Acting Commissioner of Patents and Trademarks